(12) United States Patent
Shi et al.

(10) Patent No.: US 11,109,840 B2
(45) Date of Patent: Sep. 7, 2021

(54) CALIBRATION OF ULTRASONIC ELASTICITY-BASED LESION-BORDER MAPPING

(71) Applicant: KONINKLIJKE PHILIPS N.V., Eindhoven (NL)

(72) Inventors: William Shi, Wakefield, MA (US); Ajay Anand, Fishkill, NY (US); Sheng-Wen Huang, Ossining, NY (US); Shriram Sethuraman, Woburn, MA (US); Hua Xie, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 469 days.

(21) Appl. No.: 15/562,202

(22) PCT Filed: Mar. 31, 2016

(86) PCT No.: PCT/EP2016/057152
§ 371 (c)(1),
(2) Date: Sep. 27, 2017

(87) PCT Pub. No.: WO2016/156540
PCT Pub. Date: Oct. 6, 2016

(65) Prior Publication Data
US 2018/0168552 A1 Jun. 21, 2018

Related U.S. Application Data

(60) Provisional application No. 62/140,672, filed on Mar. 31, 2015.

(51) Int. Cl.
*A61B 8/08* (2006.01)
*A61N 7/02* (2006.01)
(Continued)

(52) U.S. Cl.
CPC ............. *A61B 8/485* (2013.01); *A61B 8/085* (2013.01); *A61B 8/5223* (2013.01); *A61B 8/587* (2013.01);
(Continued)

(58) Field of Classification Search
CPC ......... A61B 8/485; A61B 8/587; A61B 8/085; A61B 8/5223; A61B 18/1477;
(Continued)

(56) References Cited

U.S. PATENT DOCUMENTS

| 5,196,343 A | 3/1993 | Zerhouni |
| 7,462,488 B2 | 12/2008 | Madsen et al. |

(Continued)

FOREIGN PATENT DOCUMENTS

| JP | 0542138 A | 2/1993 |
| WO | 2012017375 A2 | 2/2012 |

(Continued)

OTHER PUBLICATIONS

Shi, William, et al: Monitoring of radiofrequency ablation with shear save delay mapping, (2015) IEEE International Ultrasonics Symposium (IUS), IEEE, (Oct. 21, 2015) pp. 1-4.

(Continued)

*Primary Examiner* — Hien N Nguyen

(57) ABSTRACT

A medium of interest is interrogated according to ultrasound elastography imaging. A preliminary elasticity-spatial-map is formed. This map is calibrated against a reference elasticity-spatial-map that comprises an array (232) of different (240) elasticity values. The reference map is formed to be reflective of ultrasonic shear wave imaging of a reference medium. The reference medium is not, nor located at, the medium of interest, and may be homogeneous. Shear waves that are propagating in a medium are tracked by interrogating the medium. From tracking locations on opposite sides (Continued)

of an ablated-tissue border, propagation delay of a shear wave in the medium and of another shear wave are measured. The two shear waves result from respectively different pushes (128) that are separately issued. A processor decides, based on a function of the two delays, that the border crosses between the two locations. The calibrated map is dynamically updated and may include post-ablation border expansion (346) and time-annotated previous stages (344, 348).

10 Claims, 5 Drawing Sheets

(51) Int. Cl.
*A61B 8/00* (2006.01)
*A61B 18/14* (2006.01)
*A61B 18/12* (2006.01)
*A61B 17/00* (2006.01)
*A61B 18/00* (2006.01)
*A61B 18/02* (2006.01)
*A61B 18/18* (2006.01)
*A61N 7/00* (2006.01)

(52) U.S. Cl.
CPC ............ *A61B 18/1477* (2013.01); *A61N 7/02* (2013.01); *A61B 18/12* (2013.01); *A61B 2017/00106* (2013.01); *A61B 2018/00577* (2013.01); *A61B 2018/0212* (2013.01); *A61B 2018/1869* (2013.01); *A61N 2007/0052* (2013.01)

(58) Field of Classification Search
CPC .......... A61B 18/12; A61B 2017/00106; A61B 2018/00577; A61B 2018/0212; A61B 2018/1869; A61N 7/02; A61N 2007/0052
See application file for complete search history.

(56) References Cited

U.S. PATENT DOCUMENTS

| | | | |
|---|---|---|---|
| 8,118,744 | B2 | 2/2012 | Palmeri et al. |
| 2005/0054930 | A1 | 3/2005 | Rickets |
| 2010/0256530 | A1* | 10/2010 | Varghese ............... A61B 5/015 600/587 |
| 2011/0184287 | A1 | 7/2011 | Mcaleavey |
| 2013/0218012 | A1* | 8/2013 | Specht ................... A61B 8/485 600/438 |
| 2014/0005548 | A1 | 1/2014 | Fraser et al. |
| 2014/0180091 | A1 | 6/2014 | McAleavey |
| 2014/0187940 | A1 | 7/2014 | Kong |

FOREIGN PATENT DOCUMENTS

| | | | |
|---|---|---|---|
| WO | 2012080895 | A2 | 6/2012 |
| WO | 2012176100 | A1 | 12/2012 |
| WO | 2013104970 | A1 | 7/2013 |
| WO | 2014096041 | A3 | 6/2014 |

OTHER PUBLICATIONS

Arnal B. et al: Monitoring of thermal therapy based on shear modulus changes: II. Shear wave of imaging of thermal lesions, IEEE Transactions of Ultrasonics, Ferroelectrics and Frequency Control, IEEE, US, vol. 58, No. 8, (Aug. 1, 2011), pp. 1603-1611, ISSN: 0885-3010. DOI: 10. 1109/TUFFC.2011.1987 section II. "Material and Methods", "A. Experimental Setup" figures 4,5.

Zerdinetm from Computer Imaging Reference Systems, Inc. It is a solid elastic soft-tissue mimicking material in terms of speed of 35 sound and attenuation coefficient. See http://www.cirsinc.com/products/new/78/ultrasound prostate-training-phantom/?details=specs.

Guibal, A: "Evaluation of shearwave elastography for the characterisation of focal liver lesions on ultrasound", European Society of Radiology, 5 23:1138-1149 (2013).

\* cited by examiner

CALIBRATION OF ULTRASONIC ELASTICITY-BASED LESION-BORDER MAPPING

CROSS-REFERENCE TO PRIOR APPLICATIONS

This application is the U.S. National Phase application under 35 U.S.C. § 371 of International Application No. PCT/EP2016/057152, filed on Mar. 31, 2016, which claims the benefit of U.S. Provisional Patent Application No. 62/140,672, filed on Mar. 31, 2015. These applications are hereby incorporated by reference herein.

FIELD OF THE INVENTION

The present invention relates to using imaging for spatial mapping of elasticity and, more particularly, to map calibration and/or lesion border detection.

BACKGROUND OF THE INVENTION

Thermal ablation techniques, as alternatives to major surgery, are minimally invasive requiring only needles (radio-frequency (RF), cryotherapy, and microwave ablation) or non-invasive heat source such as using high-intensity focused ultrasound (HIFU). In most of the procedures, the cancerous tissue is heated to above 55° C. and coagulated.

RF ablation (RFA) is currently the only FDA approved thermal ablation therapy in the United States. It uses a probe with an active electrode tip through which a 460-500 kHz alternating electric current is conducted. The current causes ionic agitation and frictional heating. Heat is then dissipated through thermal conduction to ablate the tumor. RFA is frequently used to treat liver cancer. There are about 500,000 new cases of metastatic liver cancer in the western world and about 1 million new cases for primary liver cancer worldwide (83% of which are in developing countries). RFA and microwave ablation therapies are also gaining popularity in developing countries due to the large number of liver cancers reported (e.g., 433,000 new cases in 2009 in China alone). Current treatment protocols use the simplistic spherical ablation volume predicted from the device manufacturers' specifications. The actual treatment volumes greatly deviate from the prediction, resulting in large recurrence rates (approx. 35%).

RFA is typically performed under image guidance and monitoring. One common reason for the high recurrence rates is the inability to monitor and control ablation size to adequately kill the tumor cells. It is therefore essential to provide real-time feedback to the clinician. This can currently be achieved with reasonable accuracy with magnetic resonance (MR) based temperature imaging. However, MR imaging (MRI) is expensive and may not be readily available. As an alternative monitoring modality, ultrasound is commonly used for image guidance during placement of the needle. Due to its ease of use and wide availability it is a potentially preferred method for monitoring the lesions. However, the only way it is currently used for monitoring treatment is by visualizing the hyperechoic lesions on a B-mode image. In most cases, the hyperechogenicity is due to the formation of microbubbles during RFA which is a temporary effect and poorly correlated with the lesion boundaries. Therefore, such visualization is only approximate and not a good indicator of the treatment efficacy.

Ultrasound has been used in shear wave elastography applied to liver lesions. Guibal, A: "Evaluation of shearwave elastography for the characterisation of focal liver lesions on ultrasound", European Society of Radiology, 23:1138-1149 (2013). The Guibal study cites the advantage of providing a real-time two-dimensional quantifiable image of tissue stiffness.

It is also known that tissue stiffness changes during thermal ablation.

SUMMARY OF THE INVENTION

Because of tremendous changes in the elasticity of temperature-elevated tissue, ultrasound elasticity imaging has great potential in ablation monitoring. As the tissue necrosis threshold is reached, the tissue begins to harden and continues to do so with increased thermal exposure. By tracking this change, the therapy progress can be evaluated and the end point can be determined. Tissue stiffness can be measured using shear wave imaging. This entails the use of acoustic radiation force to generate displacement and shear waves that are then tracked to extract stiffness information. Shear waves travel faster with lower displacement in stiffer body tissue.

Shear wave imaging (SWI) for spatial elasticity mapping has great potential in monitoring thermal ablation therapy.

However, known SWI modes employed in ultrasound-based elastography are not sufficiently sensitive to accurately detect an ablated tissue boundary portion in the vicinity of a stiff medical instrument, such as an ablation needle or tine extending from the needle's electrode. Firstly, the rigidity of the instrument restricts shear wave displacement of the ablated tissue surrounding the needle. Secondly, the measurements of elasticity, e.g., shear modulus, suffer from low signal-to-noise (S/N) ratio. Furthermore, SWI sensitivity is further reduced, for small, deep lesions, if a low-frequency transducer is utilized for imaging. The low frequency imaging suffers from low spatial resolution, but higher frequencies are limited as to imaging depth penetration. The limitation is especially severe for the ablation of a lesion of more than 40 millimeters (mm) in depth and less than 15 mm in diameter, located near a critical structure (e.g., a nerve or blood vessel) that needs to be protected from ablation. Such a structure is referred to herein below as a protected structure. Also it would be difficult to delineate the expanding thermal lesion boundary with respect to the initial tumor contour.

Shear modulus based elasticity images have been produced based on local shear wave velocities that are further determined from shear wave propagation time such as time-to-peak (TTP) or time-to-peak slope (TIPS). Some of the hurdles to efficient elasticity assessment in shear modulus-based real-time monitoring of ablation are as follows: (1) it is hard to determine where is the peak of very low-displacement shear wave, (2) it is also hard to differentiate the peaks of a very fast shear wave between two neighboring points; (3) there exists even less displacement for the ablated tissue when the ablation needle is present during ablation; and (4) reflection of shear wave from the ablation needle complicates the shear wave profiles with more than one peak.

The approach proposed herein detects the lesion boundary by analyzing "the shear wave propagation in normal tissues" until the shear wave travels across the stiff lesion boundary.

An additional problem is that the ultrasound pushing field in SWI adversely affects the elasticity measurements as the ultrasound field cannot be produced with an uniform amplitude across all the depth (while it can only be focused to a single depth).

In accordance with what is proposed herein, the ultrasound field effects and/or the distortion in shear wave measurement caused by stiff instruments in the vicinity of measurement are removed, or minimized, by differencing of maps representative of spatial elasticities. Robustness to any differences that would result from the particular transducer/imager used is another benefit. The same can be said for tissue elasticity properties of the particular patient. In one embodiment, even the slight errors arising from heterogeneities in the medium being examined can be backed out via the use of difference maps.

Conventionally, elasticity maps provide a shear modulus distribution. Shear modulus, a typical metric of elasticity, is proportional to the square of the shear wave propagation speed. In what is proposed herein, dynamic monitoring avoids the need for dividing by small, hard to accurately make measurements, thereby further raising the S/N ratio. In particular propagation speed need not be computed as an intermediate value for use in calculating shear modulus.

It also should be noted that complex higher-order multi-line beamformers are not required for the proposed methods in effectively mapping the outline of thermal ablation lesions; whereas, the instant techniques are well suited even for more economical ultrasound scanners that have only a limited set of parallel tracking beams or that issue the tracking beams serially.

More specifically with regard to these highlights, in one aspect, a medium of interest is interrogated according to ultrasound elastography imaging and, based on a result of the interrogating, a preliminary elasticity-spatial-map is formed. This map is calibrated against a reference elasticity-spatial-map that comprises an array of different elasticity values. The reference map is formed to be reflective of ultrasonic shear wave imaging of a reference medium. The reference medium is not the medium of interest and is not located at the medium of interest.

In a particular sub-aspect, the reference medium is either: a) homogeneous if thermal ablation equipment does not reside within said reference medium, as in for example the use of high intensity focused ultrasound (HIFU) as the ablation method; or b) homogeneous exclusive of the equipment, if the equipment resides within said reference medium.

In another aspect, shear waves that are propagating in a medium are tracked by interrogating the medium. From tracking locations on opposite sides of an ablated-tissue border, propagation delay of a shear wave in the medium and of another shear wave are measured. The two shear waves result from respectively different pushes that are separately issued. A processor decides, based on a function of the two delays, that the border crosses between the two locations. In what is also an aspect, a medium is interrogated dynamically. An elasticity-spatial-map of the medium is dynamically generated. A difference between the map and a previously-formed elasticity-spatial-map of the medium is dynamically generated to thereby dynamically form an elasticity difference map that has, as entries, shear wave propagation delay differentials spatial location by spatial location. The difference map and/or a map derived therefrom are dynamically visualized, and/or from the difference map an ablated-tissue border is dynamically defined.

These aspects are effectively realizable in machine, method, and software form.

Details of these aspects are set forth below, with the aid of the following drawings, which are not drawn to scale.

DETAILED DESCRIPTION OF EMBODIMENTS

Figure 1:
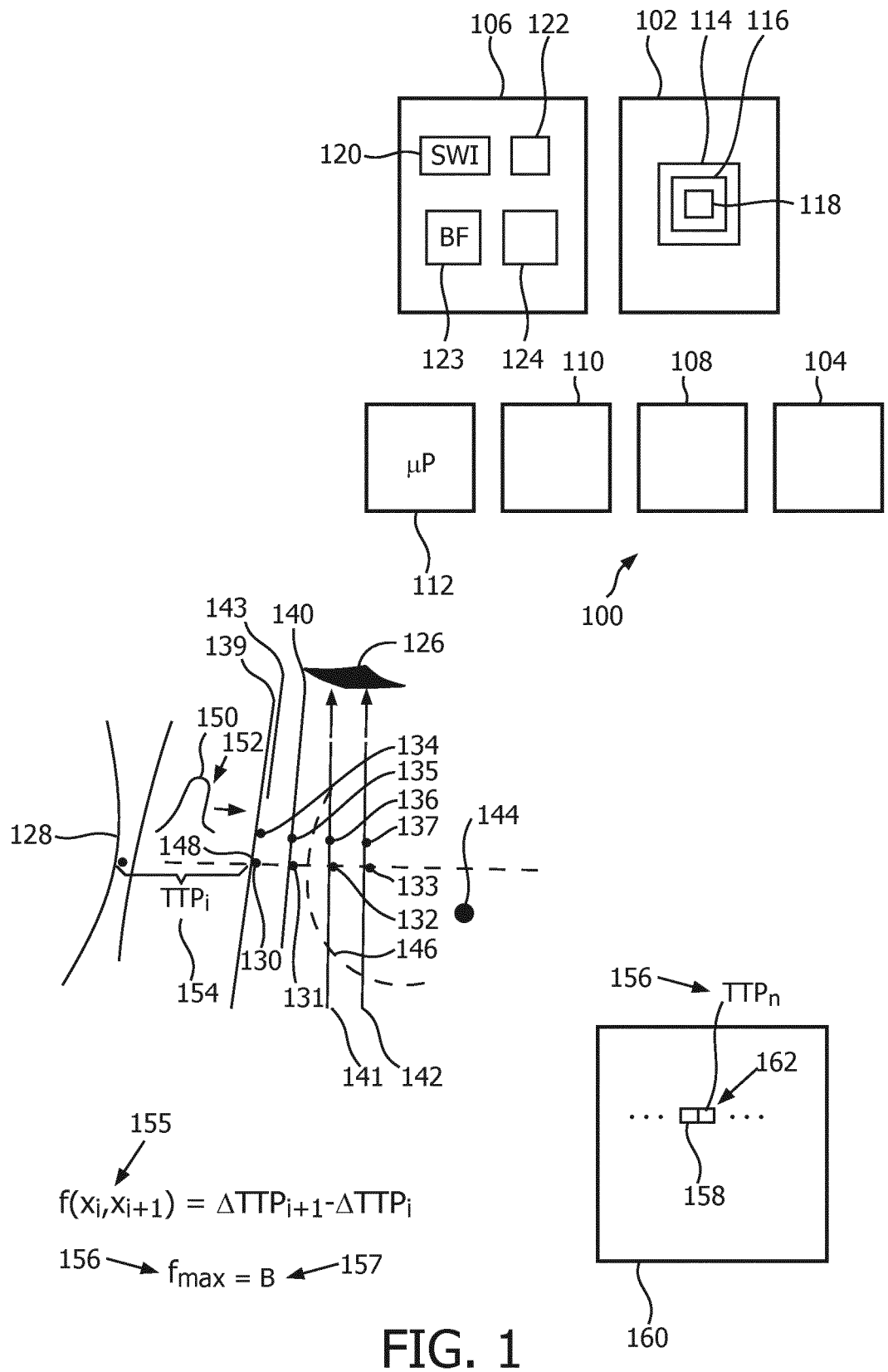
FIG. 1 is an exemplary system schematic and exemplary conceptual diagram, according to the present invention.

FIG. 1 depicts, by way of illustrative and non-limitative example, a real-time, thermal ablation monitoring elastography apparatus 100. The apparatus 100 includes an ablation device 102, an energy source 104, an imaging device 106, a display 108, user controls 110, and a microprocessor 112 or other processor such as a shear wave elastography computing unit. The microprocessor function is realizable in one or more integrated circuits. However, it could be implemented with any combination of software, firmware, and hardware.

The ablation device 102 includes, as a type of ablation equipment, an ablation needle 114. The latter includes radiofrequency (RF) electrode 116 which includes one or more tines 118 extendable into body tissue to apply heat for ablation. The energy source 104, such as the mains electrical current, provides energy for the heating. The ablation needle 114 may instead be one used for cryotherapy or microwave ablation, with an alternative corresponding construction. Optionally, the ablation may be performed by high intensity focused ultrasound (HIFU), in which case a HIFU transducer is provided instead of an ablation needle.

The imaging device 106 includes an SWI module 120, an ultrasound B-mode imaging module 122, and a beamformer 123. B-mode images may be repeatedly acquired for spatially registering elasticity readings at different stages of the ablation process. Although, the need for such registering is relieved in an off-site elasticity-spatial-map calibration embodiment discussed further below in connection with FIG. 2. The B-mode images may also serve as underlying depictions upon which color-coded, or otherwise-coded, elasticity-spatial maps (which hereinafter may simply be referred to as "elasticity maps") may be overlaid.

The imaging device 106 further includes one or more ultrasound transducers 124. Each transducer may be realized as a transducer array, i.e., array of transducer elements. Although what is proposed herein is not limited to separate transducers for pushing and imaging, separate transducers for these two functions allows tracking of the results of a push to closely follow right after the push, to thereby yield more accurate results.

A probe 126 may include the imaging transducers 124 for pushing and tracking. Optionally it may also include a HIFU therapy transducer, which may be housed in a separate probe. For creating a shear wave, the pushing transducer is operated for issuing an acoustic radiation force pushing pulse 128. The pulse is focused to a desired shear wave imaging depth, i.e., push depth. The push creates a shear wave which propagates volumetrically in all directions, although the focus may be designed to be small and narrow to accommodate tracking at multiple imaging depths. As the shear wave propagates through body tissue, it displaces the body tissue transversely to the direction of propagation. This displacement can be detected at a given tracking location 130-137 by means of a tracking pulse 139-142 directed for the location. For example, the tracking pulse 139 directed for the locations 130, 134 allows return echoes to be measured in accordance with an A-line 143. This is done repeatedly to track tissue movement along the A-line 143. As the peak of a shear wave, in the course of the wave propagation, arrives at the A-line 143, the maximum displacement of both locations 130, 134 respectively is detectable, as by repeated cross-correlation of A-lines 143 acquired from the same direction. The time between a push and the respective arrival of the peak at a monitored location 130 is known as time to peak (TTP). Tracking locations 130-137 at multiple imaging depths along a current imaging plane can monitored. From this monitoring, the TTP for the respective locations 130-137 is measureable. The propagation distances to the tracking locations are known. Since distance divided by time equals speed, a propagation speed of the shear wave can be determined with respect to the monitored location 130. This is concurrently done for various other such locations in the imaging plane. Inter-location speed differentials could thus be computed to determine local speed; however, propagation time differentials instead are computed according to what is proposed herein. Moreover, the comparisons are, according to the instant method, not only made location to location, but with a reference map. Typically, there would be many more locations 130-137, and A-lines 143 than seen in FIG. 1. Optionally a number of imaging planes, e.g., that are mutually parallel, can be monitored concurrently for three-dimensional (3D) dynamic imaging. The speed of the shear wave is related to shear modulus, which is a measure of tissue elasticity. According to what is proposed herein, propagation time differentials are calculated and utilized as indicators of tissue elasticity in a tracking location system of known geometry. For example, the tracking locations 130-137 may be arranged in an equally-spaced lattice.

In radiofrequency ablation (RFA), a tine 144 or multiple tines are deployed within a tumor, for example.

The heat created at the tine 144 ablates tissue thereby creating an ablated-tissue border 146.

A blood vessel or other protected structure 148 to be protected from adverse thermal effects of the ablation may be in the vicinity of the ablated-tissue border 146. A portion of the border 146 local to the protected structure 148 is accordingly monitored dynamically during the ablation. The real-time technique for estimation of the ablation expansion during the therapy procedure allows the clinician to adapt the therapy in order to compensate for undesired deviations of the evolving border 146 from the initially planned extent. This reduces the likelihood of tumor recurrence due to under-treatment as well as the likelihood of unwanted damage to healthy tissue.

Based on monitoring of a pair of locations 131, 132 on opposite sides of the border 146, the microprocessor 112 may decide that the border crosses between the two locations.

According to a robust, exemplary technique proposed herein, the decision is based on the monitoring of multiple locations at a given imaging depth and on comparisons to reference values. Locations at a given imaging depth are examined pairwise, the two locations being adjacent. Reference tracking for each of the two locations may have occurred at an earlier ablation stage, such as pre-ablation, or it may have been performed off-site, as on a tissue-mimicking phantom. The reference tracking, like the current tracking, yields a measure of the time lag between the push 128 and arrival of a peak 150 of a shear wave 152 at a first location 131 of the pair. This time lag is known an time to peak (TTP) 154. Other, alternative propagation delay values, such as time to peak slope (TTPS) and center of mass (COM) are usable. The reference tracking value minus the current tracking value is referred to herein as $\Delta TTP_i$. For the next location 132 of the pair, the reference tracking value minus the current tracking value is referred to herein as $\Delta TTP_{i+1}$. If the border 146 passes between the two locations i and i+1, here 131 and 132, the value of a function 155 is expected to be positive. That function $f(x_i, x_{i+1}) = \Delta TTP_{i+1} - \Delta TTPi$. Moreover, the maximum value, or "function maximum", 156, for all $f(x_i, x_{i+1})$ at the current imaging depth is denoted in FIG. 1 as $f_{max}$. If $f_{max}$ is positive, it spatially corresponds to a position through which the border 146 passes. This is represented in FIG. 1 by "B" for border 146. The microprocessor 112 can make this decision based on whether $f_{max}$ is positive. These positions can be found at multiple imaging depths, to spatially define the border 146.

The entries 158 of an elasticity map 160 are, location by location, delay values 162 such as TTP 154. For an imaging plane, the map 160 is two-dimensional. However, the map 160 may be three-dimensional for 3D monitoring of the border 146. A reference elasticity map may be formed pre-ablation from monitoring of the ablation medium or may be formed from off-site monitoring of another medium that simulates the ablation medium. A preliminary elasticity map is formed from current monitoring of the ablation medium. The reference and preliminary maps are likewise arrays of delay values 162.

A difference map, or "D-map", may be formed as a difference between the reference and preliminary maps, e.g., the reference map minus the preliminary map. The entries of a D-map are thus $\Delta TTP_i$, $\Delta TTP_{i+1}$, etc.

By offsetting or shifting the D-map by one tracking position and taking the difference between the D-map and the shifted D-map, a location-differential or "D2", map can be derived, such that the maximum values of the D2 map, where positive, spatially define a portion of the border 146. The D2 map may be color-coded to enhance visibility of the border when the map is displayed or printed. In this manner, the entire length of the border 146 in the imaging can be defined dynamically, once ablation starts to occur, throughout the subsequent monitoring. Alternatively, frame rate can be increased by confining the monitoring locally, to merely the portion of the border 146 in the vicinity of the protected structure 148. In the case of on-site calibration, i.e., of monitoring of the same physical location at different times or stages, B-mode imaging is employed to spatially register the component elasticity maps of the D-map. A number of 2D B-mode images (or a 3D image) before the ablation will be taken with landmarks (especially the tine 144) indicated. The B-mode image(s) taken during or after the ablation will be compared (e.g., via cross-correlation) to the pre-ablation images for the best match of RF data in the near field (outside the intensely heating zone). The B-mode images can be either simply formed from tracking beams or added as background images for the elasticity imaging. Off-site calibration, i.e., using a tissue-mimicking phantom, on the other hand, allows for monitoring without use of B-mode imaging to spatial register different elasticity maps to each other. In the case of on-site monitoring, the inventors have found that the D-map is, even without the extra step of B-mode-based registration, generally robust to a slight spatial mismatch of the two constituent maps.

Figure 2:
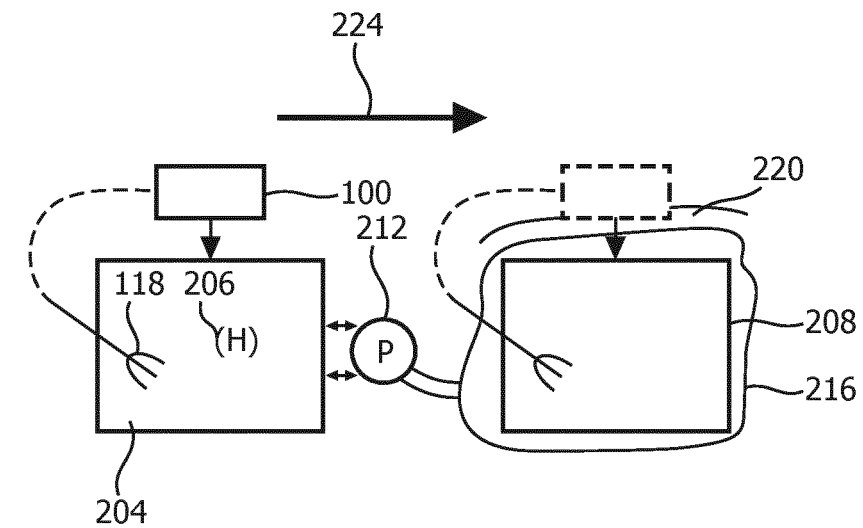
FIG. 2 is an exemplary schematic and conceptual diagram of off-site elasticity-spatial-map calibration, according to the present invention.
Figure 2:
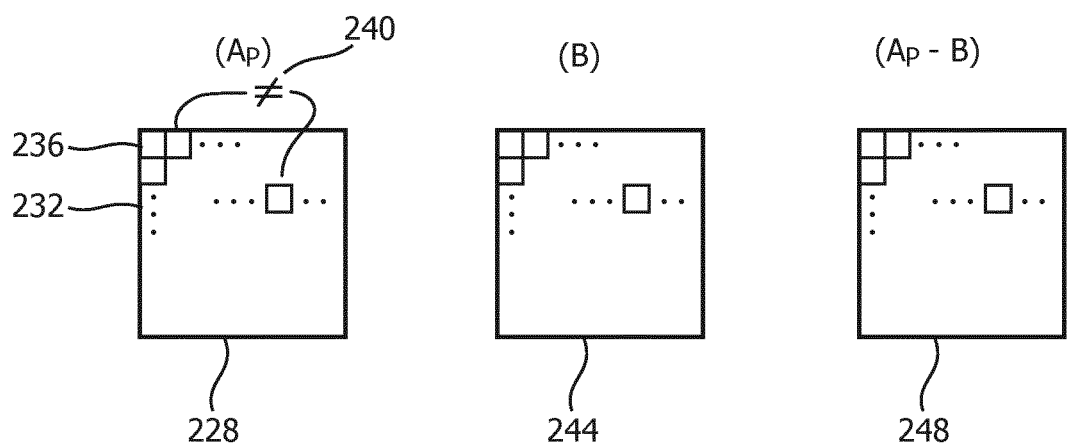
Figure 2:
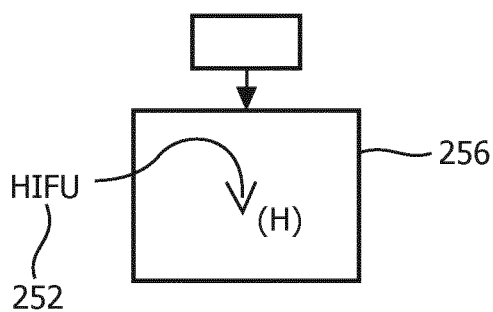

Off-site elasticity map calibration utilizes, as seen in the example of FIG. 2, a tissue-mimicking phantom 204. The material from which the phantom 204 is composed is homogeneous, as represented in FIG. 2 by the "(H)" symbol 206. The properties of the phantom are designed to be similar to those of normal tissues of a targeted organ. The elastography apparatus 100, exclusive of the ablation device 102, applies the same pushing and tracking sequences on the phantom 204 as are to be applied to the medium of interest (MOI) 208 in the clinical procedure to follow.

Thus, the phantom 204 affords a simulation of the imaging to be performed using the MOI 208.

By comparing the results from monitoring on the phantom 204 to those from monitoring on the MOI 208, the ultrasound field effects ("UFE") from monitoring can be backed out. The pushing beam is narrow at its focus, but widens gradually in the near field direction and in the far field direction. Ideally, the shear wave should be shaped like an outward cylindrical wave so that the shear wave would arrive simultaneously at all tracking locations at different depths along each tracking direction (parallel to the pushing direction). Because the ultrasound beam is not shaped ideally like a "narrow" cylinder, the effect of the imperfect shear wave source, i.e. the pushing beam, warrants correction or compensation. This distorting effect is a major part of the UFE that are backed out.

To additionally back out the distortion in the effects of the shear wave that is caused by presence of a stiff medical instrument, the phantom 204 may be provided with one or more tines 118, positioned and deployed as in the clinical treatment plan. The phantom 204 is formed with the same parenchyma 212 as that of the bodily organ 216 in which the MOI 208 is disposed. For RFA, the bodily organ is often the liver, or another organ within the body tissue 220. The arrow 224, and the dashed line outline above the MOI 208 represent the time order, in which the phantom 204 is monitored first in order to gather information to be later used in dynamic monitoring during the clinical ablation procedure.

Depicted underneath the phantom 204 in FIG. 2, a respective elasticity map 228, i.e., reference elasticity map, is formed. It is labeled ($A_p$), with "P" standing for "phantom." The reference elasticity map 228 defines an array 232 of elasticity values 236 that are shear wave propagation delays 162, as discussed herein above, except that they were derived from "off-site" monitoring, i.e., of the phantom 204. The elasticity values differ 240, as represented by the "not equal" sign, due to the effects that are being backed out by virtue of the phantom-based calibration of the clinical monitoring.

Depicted underneath the MOI 208 in FIG. 2, a respective elasticity map, i.e., preliminary elasticity map 244, is formed.

A calibrated elasticity map 248 is a D-map computed from the reference and preliminary maps 228, 244.

It is noted that, instead of RFA, HIFU may be the ablation method. This is represented in FIG. 2 by the HIFU beam 252. No thermal ablation equipment is needed inside the phantom 256. In this case, the phantom 256 is homogeneous, rather than being homogeneous exclusive of thermal ablation equipment residing within the phantom.

Alternatively, the reference map 228 may be obtained by well-known methods of numerical simulation on a model that is calibrated to experimental results obtained using a phantom. See U.S. Pat. No. 8,118,744 to Palmeri et al., paragraphs before and after Table 1; U.S. Patent Publication No. 2001/0130660 to Cloutier et al., Example 1; and U.S. Patent Publication No. 2014/0180091 to McAleavey, paragraph [0074]+. In this case too of numerical simulation, the reference medium is not, and is not located at, the MOI 208.

As to the reference map in general, whether on-site or off-site, it is representative of normal (non-ablated) body tissue having small inhomogeneities (outside stiff tumors or other stiff structures). Small inhomogeneities have relatively small effect on changes in shear wave propagation time (in comparison to the large effect of the ablated tissue or a stiff tumor), and largely can be neglected.

Figure 3:
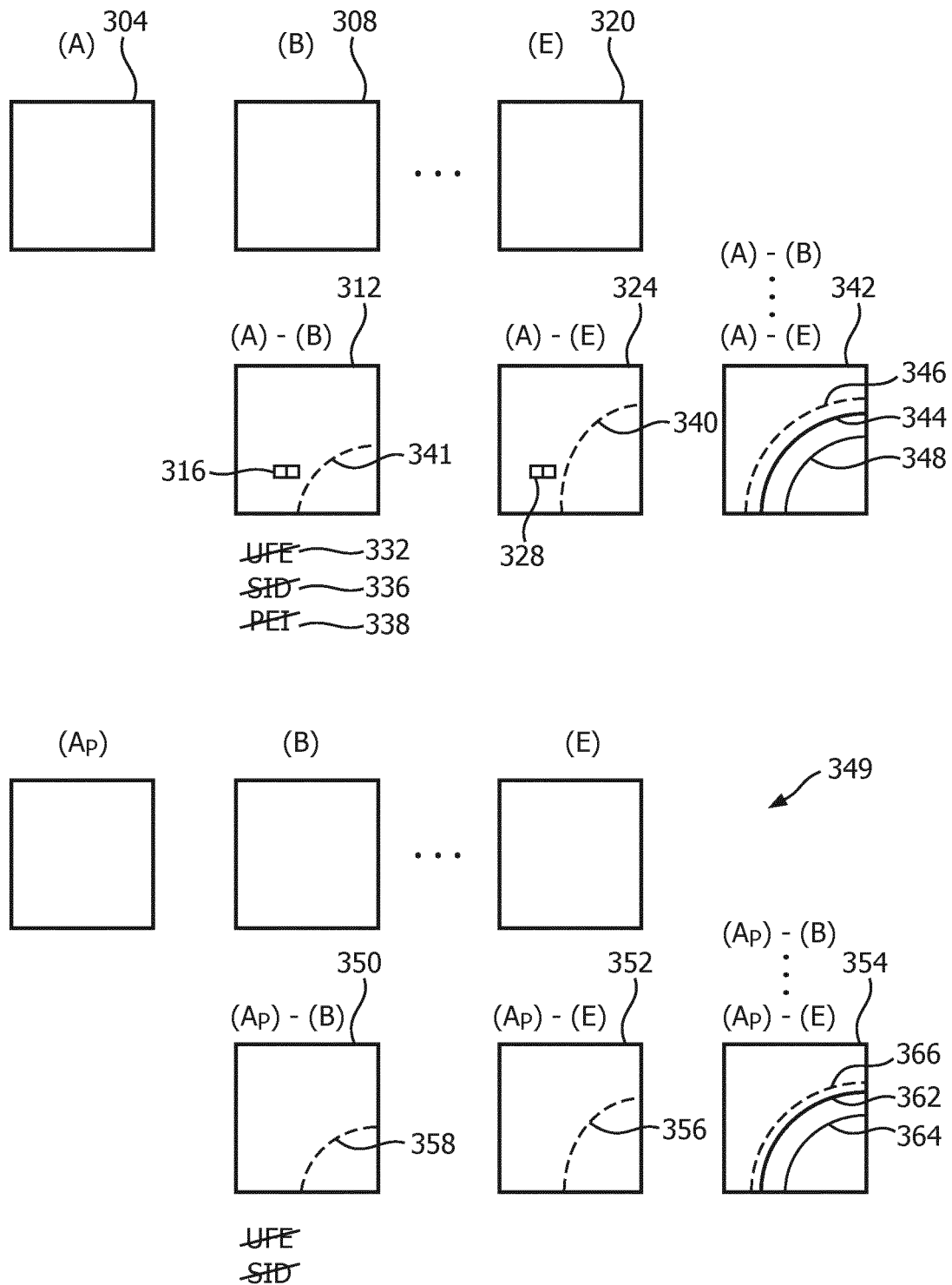
FIG. 3 is an exemplary schematic and conceptual diagram of both off-site and on-site elasticity-spatial-map calibration, including presentation and integration of difference maps, according to the present invention.

FIG. 3 relates to examples of elasticity map calibration and elasticity map presentation to the user.

With regard to on-site calibration, a number of elasticity maps are formed in a temporal sequence. A first map, which may precede any energy application or may precede any ablation, serves as a reference map 304. From the reference map 304, a subsequent elasticity map 308 at a later stage of ablation is subtracted. This yields a first D-map 312 having an array of delay differentials as respective metrics 316 of elasticity at one stage of an ablation procedure relative to elasticity at another stage of the procedure. The reference map 304 is likewise subtracted from a preliminary map 320 representative of the stage at which energy application is complete. The subtraction yields a second D-map 324 having a respective array of metrics 328 of elasticity at one stage of an ablation procedure relative to elasticity at another stage of the procedure. In any such D-maps 312, 324, or D-maps of intervening stages of ablation, ultrasound field effect (UFE) 332 and stiff instrument distortion (SID) 336 are advantageously mitigated or eliminated by the differencing that has occurred, the mitigation/elimination being represented in FIG. 3 by the cross-outs. As an additional benefit, pre-existing inhomogeneities (PEI) 338 are also mitigated or eliminated. The D-maps 312, 324 are useful as a dynamic display or printout, or as an overlay or juxtaposition to a current B-mode image, in monitoring the ablation. A dashed-line division 340 in the second D-map 324 is not necessarily presented, but represents where color coding, for instance, suggests a portion of the ablated-tissue border 146. A dashed-line division 341 in the earlier map 312 is also seen in FIG. 3.

Alternatively or in addition, from one or more D-maps 312, 324, respective D2-maps can be formed, and presented to the user.

As another refinement, post-energy-application thermal effects can be built into the D-maps 312, 324 or D2-maps, by continuing to tracking post-ablation. A map 342 formed some time after cutting off the energy source for ablation retains the division 340 as a solid line 344. A dashed-line division 346 corresponds to the previous dashed-line division 340, but shows slight expansion in the ablation zone that has occurred in the post-ablation-energy-source-application period. Another solid line 348 retains the earlier dashed-line division 341. Any of the solid lines 344, 348 may be presented to the user as an overlay graphic. Alternatively, the integration of the progressive maps may be presented visually as a loop of frames, each frame showing the D-map or D2-map of a next stage. The progressive maps or the solid lines 344, 348 may be annotated with the then-current ablation time or other indicator of the then-current ablation stage, as a visual aid to the clinician in estimating an extent of ablation border expansion.

Alternatively or in addition, the automatic tracking of the location of the border 340 may be performed. The clinician may be continually notified, audibly or by onscreen message, of a distance between the border 340 and a critical structure 148 automatically identified, or previously identified by the clinician, in intermittent real-time B-mode imaging. Heat generation by ablation device 102 may automatically be halted by the microprocessor 112 monitoring the ablation, in the event a critical-structure proximity threshold is met. The border-to-critical-structure distance could continue to be determined post-heat-generation by taking into account the post-energy-application thermal effects, i.e., monitoring the continued expansion of the border 146 for a limited time.

For the off-site elasticity map calibration implementation, analogous mapping applies. Elasticity maps 349 are formed for different stages of the ablation procedure. The on-site maps 312, 324, 342 correspond to the off-site maps 350, 352, 354. The on-site divisions 340, 341, 346 correspond to the off-site divisions 356, 358, 366. The on-site solid lines 344, 348 correspond to the off-site solid lines 362, 364.

Operationally with respect to off-site calibration, the bodily organ 216 to be subjected to ablation is selected (main routine 400, step S402). The homogeneous, tissue-mimicking phantom 204 is created that simulates the parenchyma 212 of the selected organ 216 (step S404). An example of a material for a phantom used for simulating liver tissue in ultrasound imaging is ZERDINE™ from COMPUTER IMAGING REFERENCE SYSTEMS, INC. It is a solid elastic soft-tissue mimicking material in terms of speed of sound and attenuation coefficient. See http://www.cirsinc.com/products/new/ultrasound-prostate-training-phantom/?details=specs; see also U.S. Patent Publication No. 2005/0054930 to Rickets et al., FIGS. 6(a)-6(c): sonoelastographic images using a liver phantom; see also U.S. Pat. No. 7,462,488 to Madsen et al., entitled "Tissue mimicking elastography phantoms", the entire disclosure of which is incorporated herein by reference. After these preparatory steps, or as an entry point, shown as "A" in FIG. 4, for on-site calibration, the ablation needle 114 is inserted into the phantom 204 to the clinical treatment depth (step S408). Here, the assumption is that RFA will be the clinical procedure and that an ablation needle will be utilized. The tines 118 are deployed (step S410). The transmit function in the beamformer 123 is focused to a targeted push location (step S412). The pushing pulse 128 is applied to create a shear wave (step S416). Transmit and receive beamforming via the beamformer 123 is adjusted for acquisition of a current A-line 143 (step S420). A tracking pulse 136, 138 issues (step S422). The A-line 143 is acquired (step S424). If another A-line 143 is to be acquired (step S426), return is made to the A-line acquisition step S420. Otherwise, if no other A-line 143 is to be acquired (step S426), but another pushing pulse 128 is to be emitted (step S430), return is made to the push focusing step S412. Otherwise, if there is no further pushing pulse 128 to issue (step S430), monitoring is completed. In this example, serial beamforming is cited, although the tracking may occur instead in parallel using a multiline beamformer. As mentioned herein above, the serial receive beamforming and sparse parallelism of more economical ultrasound systems are feasible in view of the above cited efficiencies of what is proposed herein above.

Figure 4:
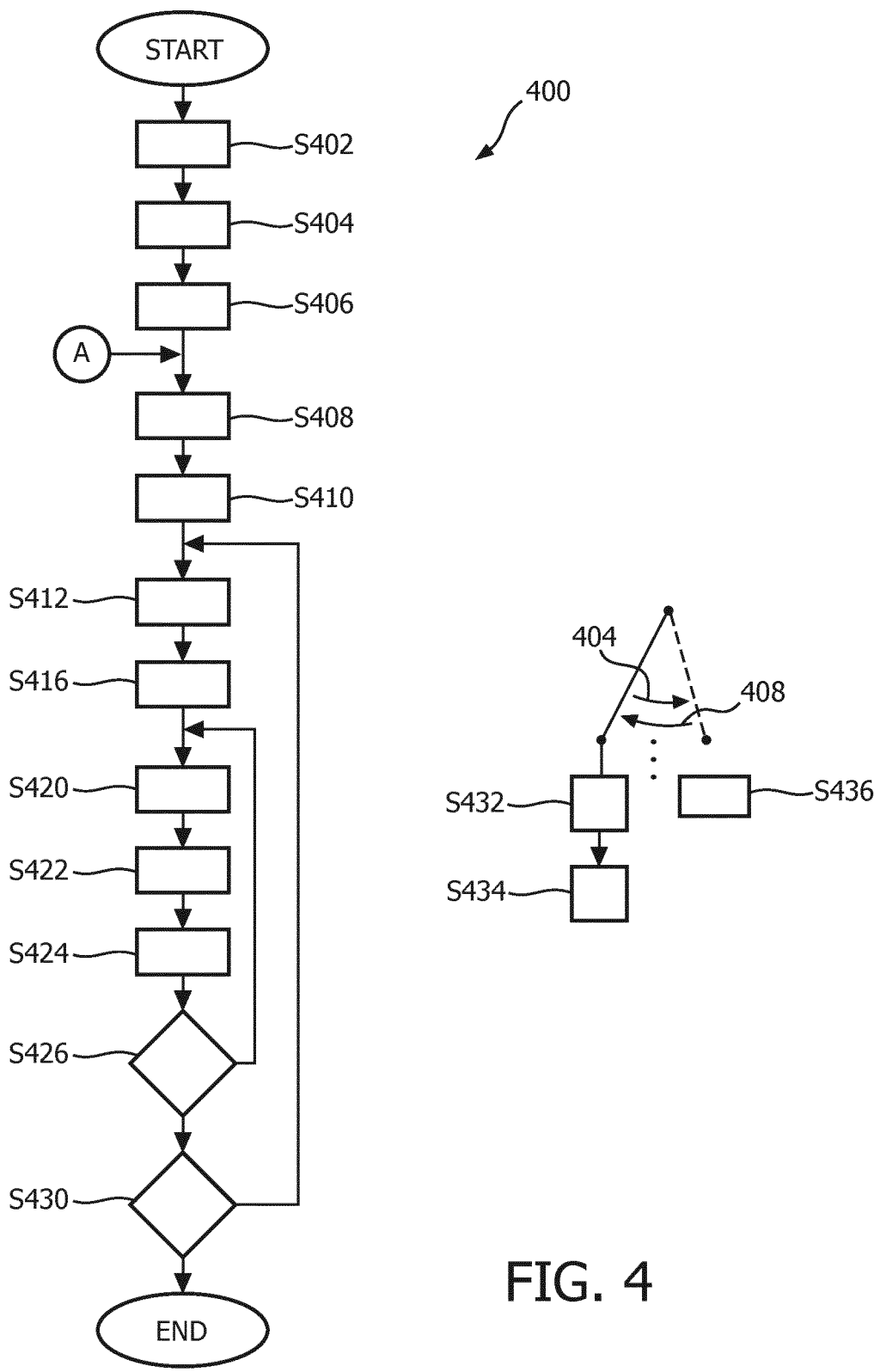
FIGS. 4 and 5 are exemplary flow charts of system implementation and operation, in accordance with the present invention.

For the on-site mode or implementation, processing alternates, as represented by the oppositely, directed arrows 404, 408 in FIG. 4, between pushing S432 and tracking S434, and acquiring a B-mode image S436.

Figure 5:
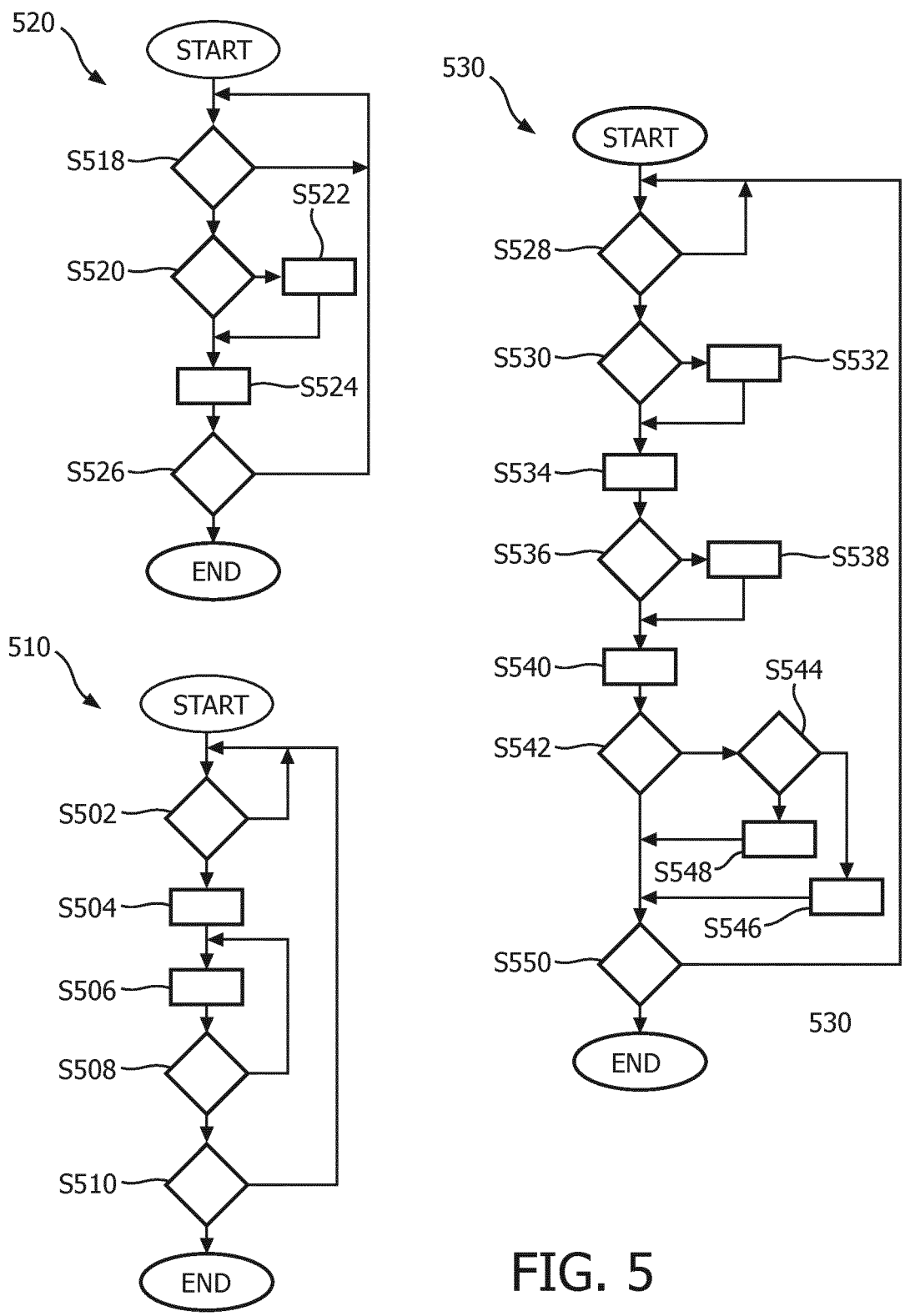

Concurrent with the main routine 400 and in accordance with an elasticity map formation routine 510 as presented in FIG. 5, when tracking data is available (step S502), processing points to a first tracking location (step S504). TTP is computed or retrieved from storage (step S506). If there is a next tracking location to process for forming a current preliminary elasticity map (step S508), return is made to the TTP computation/retrieval step S506. Otherwise, if there is no further tracking location for forming a current preliminary elasticity map (step S508), and if ablation monitoring is to continue (step S510), return is made to step S502.

Also concurrent with the main routine 400, is a D-map formation routine 520. When a preliminary elasticity map 244, 308, 320 and its respective reference elasticity map 228, 304 are available (step S518), the processing depends on whether the mode or implementation is off-site (step S520). If it is off-site (step S520), respective B-mode images formed from the tracking data upon which the reference and preliminary maps are based are cross-correlated, for the best match in the near field, in order to spatially co-register the reference and preliminary maps (step S522). The preliminary map 244, 308, 320 is subtracted from the reference map 228, 304 to form a D-map (step S524). The maximum positive value at each tracking depth, i.e., row, of the D-map can be marked for optional highlighting or other distinguishing in the dynamic presentation. If ablation monitoring is to continue (step S526), return is made to the map availability checking step S518.

A map presentation routine 530 also runs concurrently. When a D-map becomes available (step S528), processing depends on whether a D2-map is to be formed from it (step S530). If a D-2 map is to be formed (step S530), the D-2 map is derived (step S532). In either case, the ablated-tissue border 146 is spatially defined (step S534). Proximity to a protected structure 148 is checked (step S536). If proximity is below a predetermined threshold (step S536), the user is notified (step S538). In either case, the D-map and/or D2 map is displayed or printed, along with any optional highlighting or distinguishing of the current border 146 of the ablated tissue (step S540). If a series one or more temporally-previous stage maps are to be presented (step S542), processing depends on whether the stage(s) is to be presented as a screen graphic overlay (step S544). If the stage(s) are to be presented as a screen graphic overlay (step S544), the overlay(s) are sent to screen (step S546). Otherwise, if the stage(s) is not to be presented as a screen graphic overlay (step S544), a loop of D-maps/D-2 maps of previous stages is presented onscreen (step S548). If an offset D-map is to be displayed, the D-map that has just become available is offset laterally by one A-line, the difference between the D-map and its offset is taken, and the resulting, or "D2", map is presented visually. If temporally-previous stage maps are not to be presented (step S542) or at the conclusion of either step S546 or S548, processing depends on whether ablation tracking is complete (step S550). If ablation tracking is not complete (step S550), processing branches back to step S528.

A medium of interest is interrogated according to ultrasound elastography imaging. A preliminary elasticity-spatial-map is formed. This map is calibrated against a reference elasticity-spatial-map that comprises an array of different elasticity values. The reference map is formed to be reflective of ultrasonic shear wave imaging of a reference medium. The reference medium is not, nor located at, the medium of interest, and may be homogeneous. Shear waves that are propagating in a medium are tracked by interrogating the medium. From tracking locations on opposite sides of an ablated-tissue border, propagation delay of a shear wave in the medium and of another shear wave are measured. The two shear waves result from respectively different pushes that are separately issued. A processor decides, based on a function of the two delays, that the border crosses between the two locations. The calibrated map is dynamically updated and may include post-ablation border expansion and time-annotated previous stages.

While the invention has been illustrated and described in detail in the drawings and foregoing description, such illustration and description are to be considered illustrative or exemplary and not restrictive; the invention is not limited to the disclosed embodiments.

For example, real time monitoring of, for example, a small, deep ablation zone may entail monitoring the entire two- or three-dimensional border rather than just a portion local to protected structure.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The word "exemplary" is used herein to mean "serving as an example, instance or illustration." Any embodiment described as "exemplary" is not necessarily to be construed as preferred or advantageous over other embodiments and/or to exclude the incorporation of features from other embodiments. Any reference signs in the claims should not be construed as limiting the scope.

A computer program can be stored momentarily, temporarily or for a longer period of time on a suitable computer-readable medium, such as an optical storage medium or a solid-state medium. Such a medium is non-transitory only in the sense of not being a transitory, propagating signal, but includes other forms of computer-readable media such as register memory, processor cache and RAM.

A single processor or other unit may fulfill the functions of several items recited in the claims. The mere fact that certain measures are recited in mutually different dependent claims does not indicate that a combination of these measures cannot be used to advantage.

What is claimed is:

1. A tissue ablation imaging apparatus coupled to an ultrasound elastography imaging device, the coupled apparatus and device comprising:
    an ultrasound scanner;
    a shear wave elastography processor configured to operate said ultrasound scanner to interrogate a medium of interest and form a preliminary elasticity-spatial-map based, at least in part, on a result of the interrogating, wherein the shear wave elastography processor is further configured to determine a calibrated elasticity-spatial-map by subtracting the preliminary elasticity-spatial-map from a reference elasticity-spatial-map comprising an array of different elasticity values corresponding to a reference medium that is not, nor is located at, said medium of interest, the preliminary elasticity-spatial-map and the reference elasticity-spatial-map being formed in a temporal sequence;
    an ablation imaging device configured for tracking shear waves that are propagating in the medium of interest; and
    an ablation imaging processor configured to, in response to instructions on said imaging apparatus, perform the following steps of
        operating said ablation imaging device to interrogate the medium of interest,
        measuring, from tracking locations on opposite sides of an ablated-tissue border, a propagation delay of a first shear wave in the medium of interest and of a second shear wave, the first and second shear waves resulting from respectively different pushes that are separately issued, and,
        based on a function of the propagation delay of the first shear wave and the propagation delay of the second shear wave, deciding whether said border crosses between the two tracking locations.

2. The coupled apparatus and device of claim 1, said reference medium comprising a tissue-mimicking phantom configured to simulate a parenchyma of a particular bodily organ.

3. The coupled apparatus and device of claim 1, wherein said reference medium is either: a) homogeneous if thermal ablation equipment does not reside within said reference medium; or b) homogeneous exclusive of said equipment, if said equipment resides within said reference medium.

4. The coupled apparatus and device of claim 3, said equipment residing within said reference medium is configured to simulate presence of said equipment within said medium of interest.

5. The coupled apparatus and device of claim 1, wherein said different elasticity values comprise shear wave propagation delay values.

6. The coupled apparatus and device of claim 5, wherein said shear wave propagation delay values comprise respective time periods in shear wave propagation to respective locations in said reference medium.

7. The coupled apparatus and device of claim 5, wherein said preliminary elasticity-spatial-map comprises shear wave propagation delay values.

8. The coupled apparatus and device of claim 1, configured such that the deciding is made without need for dividing distance by propagation delay.

9. The coupled apparatus and device of claim 1, wherein the ablation imaging processor, in response to instructions on said imaging apparatus, is further configured to track said first shear wave to form said reference elasticity-spatial-map and to track said second shear wave to form the preliminary elasticity-spatial-map.

10. The coupled apparatus and device of claim 9, wherein the ablation imaging processor, in response to instructions on said imaging apparatus, is further configured to compare the reference elasticity-spatial-map and the preliminary elasticity-spatial map to form a difference map, and to carry out at least one of the following (1) generating images for visualizing one or more of said difference map and a map derived from said difference map; and (2) defining, from said difference map, an ablated-tissue border.

* * * * *